(12) United States Patent
Poremba

(10) Patent No.: US 10,980,572 B1
(45) Date of Patent: Apr. 20, 2021

(54) TICK REMOVAL AND ENCAPSULATION DEVICE AND METHOD

(71) Applicant: Barbara Poremba, Lynn, MA (US)

(72) Inventor: Barbara Poremba, Lynn, MA (US)

(*) Notice: Subject to any disclaimer, the term of this patent is extended or adjusted under 35 U.S.C. 154(b) by 0 days.

(21) Appl. No.: 16/919,060

(22) Filed: Jul. 1, 2020

(51) Int. Cl.
*A61B 17/50* (2006.01)

(52) U.S. Cl.
CPC ........ *A61B 17/50* (2013.01); *A61B 2017/505* (2013.01)

(58) Field of Classification Search
CPC .......... A61B 17/0483; A61B 17/06061; A61B 17/08; A61B 17/083; A61B 17/085; A61B 17/30; A61B 17/50; A61B 17/122; A61B 17/128; A61B 17/1285; A61B 2017/301; A61B 2017/303; A61B 2017/305; A61B 2017/505; A61B 2017/320064; A45D 26/0066; A01M 3/04; A01M 1/02; A01M 1/14; Y02A 50/375; A61M 25/02; A61M 2025/0273; A61M 2025/028
See application file for complete search history.

(56) References Cited

U.S. PATENT DOCUMENTS

| 1,087,058 | A | * | 2/1914 | Zielfeldt | A01M 1/14 43/114 |
|---|---|---|---|---|---|
| 4,217,722 | A | * | 8/1980 | McMullen | A01M 1/14 43/114 |
| 5,607,451 | A | * | 3/1997 | Menocal, Jr. | A45D 26/0066 294/99.2 |
| 5,634,293 | A | * | 6/1997 | Mike | A01M 1/14 43/114 |
| 2002/0112395 | A1 | * | 8/2002 | Marsh | A01M 1/14 43/114 |
| 2004/0148847 | A1 | * | 8/2004 | Jacobson | A01M 1/14 43/114 |
| 2012/0110893 | A1 | * | 5/2012 | Fabry | A01M 1/14 43/114 |
| 2014/0290123 | A1 | * | 10/2014 | Duff | A01M 1/14 43/114 |

* cited by examiner

*Primary Examiner* — Diane D Yabut
*Assistant Examiner* — Christian D Knauss
(74) *Attorney, Agent, or Firm* — Daniel N. Smith

(57) ABSTRACT

A cost-effective, small, light-weight, portable thin strip device for quickly, safely, effectively, easily, hygienically removing ticks attached to skin. The device comprises a tick engagement section, and two adhesive sections foldable onto the tick and the tick engagement section. The device is configured to encapsulate and preserve the removed tick in a clear, viewable position for medical inspection and eventual disposal. The device enables the catch and encapsulation of ticks without physically touching or handling the ticks directly.

9 Claims, 12 Drawing Sheets

TICK REMOVAL AND ENCAPSULATION DEVICE AND METHOD

FIELD OF THE INVENTION

The field of the invention relates to a device for safely removing ticks from a user's skin that is configured to encapsulate and preserve the removed tick for inspection and eventual disposal.

BACKGROUND OF INVENTION

Ticks are troublesome insects that easily attach to the skin upon contact in wooded or other natural environments. Upon contact, the ticks latch onto the skin and can be difficult, if not painful to remove, particularly for individuals who are afraid of, or repulsed by ticks. Leaving the tick on the skin is not an option, as they carry pathogens that can eventually sicken the human or animal host.

The population and geographic spread of ticks has expanded in recent decades, leading to an expansion of tick-borne sicknesses and diseases in humans and animals.

Another problem is encapsulation and preservation of the tick after removal from the skin. Once a host has been infected by a tick, it's important for medical personnel to view, and possibly test the tick for any diseases that may have been passed to the animal or human hosts, so preventative treatment measures can be determined and implemented.

Previous devices remove ticks from the skin, but do not provide readily available means of rapidly, effectively, and hygienically removing, encapsulating, and preserving ticks for medical inspection and eventual disposal. Moreover, such devices often fail to adequately seal exposed adhesive surfaces on the device after tick contact, adhesion, and encapsulation. This is necessary to prevent future coincidental adhesive contact with surrounding surfaces or objects. Previous devices also fail to prevent removed ticks from being exposed to surroundings for possible physical contact by humans and animals.

The subject invention provides a cost-effective, small, light-weight, portable device for easily and rapidly removing ticks from skin, and encapsulating and preserving them in a clear, viewable position for inspection of pathogens by medical personnel. The device of the subject invention enables the catch and encapsulation of ticks without physically touching or handling the ticks directly.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a device configured to remove and encapsulate ticks, the device comprising: a substantially rigid strip comprising a substantially flat top surface, a substantially flat bottom surface, a distal end section, a middle section, a proximal end section, a first foldable indentation between the distal end section and the middle section, and a second foldable indentation between the middle section and the proximal end section; wherein the middle section and the proximal end section comprise adhesive on the top surface; wherein the distal end section of the strip is configured to be positioned proximate to the tick on skin, and further configured to be gradually moved in a distal direction underneath and in contact with the tick on the skin until at least a portion of the distal end section is underneath the tick; wherein the strip is configured to fold at the first and second foldable indentations as the middle section and the proximal end section are moved in a distal direction over the tick onto the distal end section; wherein the adhesive on the middle section is configured to be pressed onto and adhere to the tick and the top surface of distal end section; wherein the device is configured to permit the user to firmly pull the device and adhered tick straight up and away from the skin; and wherein the adhesive on the proximal end section is configured to fold over and adhere to the tick and the bottom surface of the distal end section of the strip.

The subject invention also discloses a device configured to remove and encapsulate ticks, the device comprising: a substantially rigid strip comprising a substantially flat top surface, a substantially flat bottom surface, a distal end section, a middle section, a proximal end section, a first foldable indentation between the distal end section and the middle section, and a second foldable indentation between the middle section and the proximal end section; wherein the middle section and the proximal end section comprise adhesive on the top surface; wherein the distal end section of the strip is configured to be positioned proximate to the tick on skin, and further configured to be gradually moved in a distal direction underneath and in contact with the tick on the skin until at least a portion of the distal end section is underneath the tick; wherein the strip is configured to fold at the first and second foldable indentations as the middle section and the proximal end section are moved in a distal direction over the tick onto the distal end section; wherein the adhesive on the middle section is configured to be pressed onto and adhere to the tick and the top surface of distal end section; wherein the device is configured to permit the user to firmly pull the device and adhered tick straight up and away from the skin without the user physically touching the tick directly; wherein the adhesive on the proximal end section is configured to fold over and adhere to the tick and the bottom surface of the distal end section of the strip; and wherein the device preserves the removed tick in a clear, viewable position for medical inspection and eventual disposal.

The subject invention further discloses a device configured to remove and encapsulate ticks, the device comprising: a substantially rigid strip comprising a substantially flat top surface, a substantially flat bottom surface, three discrete sections, and two foldable indentations between the three discrete sections; wherein the two of the three discrete sections comprise adhesive on the top surface; wherein the distal end of the strip is configured to be positioned proximate to the tick on skin, and further configured to be gradually moved in a distal direction underneath and in contact with the tick on the skin until at least a portion of the distal end is underneath the tick; wherein the strip is configured to fold at the two foldable indentations as two of the three discrete sections are moved in a distal direction over the tick onto the distal end of the strip; wherein the adhesive on the discrete sections is configured to be pressed onto and adhere to the tick and the top surface and bottoms surfaces of distal end section; and wherein the device is configured to permit the user to firmly pull the device and adhered tick straight up and away from the skin.

The subject invention discloses a device configured to remove and encapsulate ticks, the device comprising: a substantially rigid strip comprising a substantially flat top surface, a substantially flat bottom surface, three discrete sections, and two foldable indentations between the three discrete sections; wherein the two of the three discrete sections comprise adhesive on the top surface; wherein the distal end of the strip is configured to be positioned proximate to the tick on skin, and further configured to be gradually moved in a distal direction underneath and in contact with the tick on the skin until at least a portion of the distal end is underneath the tick; wherein the strip is configured to fold at the two foldable indentations as two of the three discrete sections are moved in a distal direction over the tick onto the distal end of the strip; wherein the adhesive on the discrete sections is configured to be pressed onto and adhere to the tick and the top surface and bottoms surfaces of distal end section; wherein the device is configured to permit the user to firmly pull the device and adhered tick straight up and away from the skin, without the user physically touching the tick directly; and wherein the device preserves the removed tick in a clear, viewable position for medical inspection and eventual disposal.

The subject invention also discloses tick removal and containment device comprising: a thin strip with a substantially flat top surface, a substantially flat bottom surface, a distal end, and a proximal end, wherein the thin strip comprises a substantially rigid first section, a substantially rigid second section, and a substantially rigid third section separated by first and second foldable lateral indentations; wherein the first section is on the distal end of the thin strip and a proximal end of the first section comprises the first foldable indentation, further wherein the first section comprises no adhesives; a notch on a distal end of the first section, wherein the notch comprises a substantially triangular shape; wherein a distal end of the second section comprises the first foldable lateral indentation, and a proximal end of the second section comprises the second foldable lateral indentation wherein the top surface of the second section comprises an adhesive with a first peelable flexible cover and a first peel tab; wherein the third section is on the proximal end of the thin strip, wherein a distal end of the third section comprises the second foldable lateral indentation, wherein the top surface of the third section comprises an adhesive with a second peelable flexible cover and a second peel tab; wherein to remove a tick, the device is configured to be held in a user's hands with the notch positioned proximate to the tick on skin, wherein a tip of the triangular shaped notch is configured to be gradually moved in a distal direction underneath and in contact with the tick on the skin until at least a portion of the first section is underneath the tick; wherein once the first section is at least partially underneath the tick, the first peelable flexible cover is removed from the second section using the first peel tab, and the second peelable flexible cover is removed from the third section using the second peel tab; wherein the second section and the third sections are configured to both fold at the first and second foldable lateral indentations in a distal direction over the tick onto the first section; wherein the exposed adhesive on the top surface of the third section is configured to be pressed onto and adhere to the tick and the top surface of first section; wherein the device is configured to permit the user to firmly pull the device and adhered tick straight up and away from the skin; and wherein the exposed top surface adhesive of the third section is configured to fold over at the second foldable lateral indentation in the distal direction and pressed onto and adhere to the tick and the bottom surface of the first section.

The subject invention further discloses tick removal and containment device comprising: a thin strip with a substantially flat top surface, a substantially flat bottom surface, a distal end, and a proximal end, wherein the thin strip comprises a substantially rigid first section, a substantially rigid second section, and a substantially rigid third section separated by first and second foldable lateral indentations; wherein the first section is on the distal end of the thin strip and a proximal end of the first section comprises the first foldable indentation, further wherein the first section comprises no adhesives; a notch on a distal end of the first section, wherein the notch comprises a substantially triangular shape; wherein a distal end of the second section comprises the first foldable lateral indentation, and a proximal end of the second section comprises the second foldable lateral indentation wherein the top surface of the second section comprises an adhesive with a first peelable flexible cover and a first peel tab; wherein the third section is on the proximal end of the thin strip, wherein a distal end of the third section comprises the second foldable lateral indentation, wherein the top surface of the third section comprises an adhesive with a second peelable flexible cover and a second peel tab; wherein to remove a tick, the device is configured to be held in a user's hands with the notch positioned proximate to the tick on skin, wherein a tip of the triangular shaped notch is configured to be gradually moved in a distal direction underneath and in contact with the tick on the skin until at least a portion of the first section is underneath the tick; wherein once the first section is at least partially underneath the tick, the first peelable flexible cover is removed from the second section using the first peel tab, and the second peelable flexible cover is removed from the third section using the second peel tab; wherein the second section and the third sections are configured to both fold at the first and second foldable lateral indentations in a distal direction over the tick onto the first section; wherein the exposed adhesive on the top surface of the third section is configured to be pressed onto and adhere to the tick and the top surface of first section; wherein the device is configured to permit the user to firmly pull the device and adhered tick straight up and away from the skin without the user physically touching the tick directly; wherein the exposed top surface adhesive of the third section is configured to fold over at the second foldable lateral indentation in the distal direction and pressed onto and adhere to the tick and the bottom surface of the first section; and wherein the device preserves the removed tick in a clear, viewable position for medical inspection and eventual disposal.

The subject invention also discloses a device configured to remove and encapsulate ticks, the device comprising: a substantially rigid thin strip comprising a substantially flat top surface, a substantially flat bottom surface, a distal end, a proximal end, three discrete sections, and two foldable indentations separating the three discrete sections; wherein the distal end of the thin strip comprises one of the three discrete sections and a notch configured to slide underneath and hold a tick; a middle portion of the thin strip comprising another of the three discrete sections with one foldable indentation on the distal side of the middle portion and the other foldable indentation on the proximal side, wherein the top surface of the middle portion comprises an adhesive; wherein the proximal end of the thin strip comprises the third of the three discrete sections, wherein the top surface of the proximal end comprises an adhesive; wherein the device is configured to be positioned with the notch proximate to the tick on skin, and further configured to permit the notch to be gradually moved in a distal direction underneath and in contact with the tick on the skin until at least a portion of the distal end of the thin strip is underneath the tick; wherein the thin strip is configured to fold at the two foldable indentations as the middle portion and proximal end of the thin strip are moved in a distal direction over the tick onto the distal end of the thin strip; wherein the adhesive on middle portion is configured to be pressed onto and adhere to the tick and the top surface of distal end of the thin strip; wherein the device is configured to permit the user to firmly pull the device and adhered tick straight up and away from the skin; and wherein the top surface adhesive of the proximal end of the thin strip is configured to fold over and adhere to the tick and the bottom surface of the distal end of the thin strip.

The subject invention discloses a device configured to remove and encapsulate ticks, the device comprising: a substantially rigid thin strip comprising a substantially flat top surface, a substantially flat bottom surface, a distal end, a proximal end, three discrete sections, and two foldable indentations separating the three discrete sections; wherein the distal end of the thin strip comprises one of the three discrete sections and a notch configured to slide underneath and hold a tick; a middle portion of the thin strip comprising another of the three discrete sections with one foldable indentation on the distal side of the middle portion and the other foldable indentation on the proximal side, wherein the top surface of the middle portion comprises an adhesive; wherein the proximal end of the thin strip comprises the third of the three discrete sections, wherein the top surface of the proximal end comprises an adhesive; wherein the device is configured to be positioned with the notch proximate to the tick on skin, and further configured to permit the notch to be gradually moved in a distal direction underneath and in contact with the tick on the skin until at least a portion of the distal end of the thin strip is underneath the tick; wherein the thin strip is configured to fold at the two foldable indentations as the middle portion and proximal end of the thin strip are moved in a distal direction over the tick onto the distal end of the thin strip; wherein the adhesive on middle portion is configured to be pressed onto and adhere to the tick and the top surface of distal end of the thin strip; wherein the device is configured to permit the user to firmly pull the device and adhered tick straight up and away from the skin without the user physically touching the tick directly; wherein the top surface adhesive of the proximal end of the thin strip is configured to fold over and adhere to the tick and the bottom surface of the distal end of the thin strip; and wherein the device preserves the removed tick in a clear, viewable position for medical inspection and eventual disposal.

The subject invention further discloses a device configured to remove and encapsulate ticks, the device comprising: a substantially rigid strip comprising a substantially flat top surface, a substantially flat bottom surface, a distal end, a proximal end, three discrete sections, and two foldable indentations separating the three discrete sections; wherein the distal end of the strip comprises one of the three discrete sections and is configured to slide underneath and hold a tick; a middle portion of the strip comprising another of the three discrete sections with one foldable indentation on the distal side of the middle portion and the other foldable indentation on the proximal side, wherein the top side of the middle portion comprises an adhesive; wherein the proximal end of the strip comprises the third of the three discrete sections, wherein the top surface of the proximal end comprises an adhesive; wherein the distal end of the strip is configured to be positioned proximate to the tick on skin, and further configured to be gradually moved in a distal direction underneath and in contact with the tick on the skin until at least a portion of the distal end of the strip is underneath the tick; wherein the strip is configured to fold at the two foldable indentations as the middle portion and proximal end of the strip are moved in a distal direction over the tick onto the distal end of the strip; wherein the adhesive on middle portion is configured to be pressed onto and adhere to the tick and the top surface of distal end of the strip; wherein the device is configured to permit the user to firmly pull the device and adhered tick straight up and away from the skin; and wherein the top surface adhesive of the proximal end of the strip is configured to fold over and adhere to the tick and the bottom surface of the distal end of the strip.

The subject invention additionally discloses a device configured to remove and encapsulate ticks, the device comprising: a substantially rigid strip comprising a substantially flat top surface, a substantially flat bottom surface, a distal end, a proximal end, three discrete sections, and two foldable indentations separating the three discrete sections; wherein the distal end of the strip comprises one of the three discrete sections and is configured to slide underneath and hold a tick; a middle portion of the strip comprising another of the three discrete sections with one foldable indentation on the distal side of the middle portion and the other foldable indentation on the proximal side, wherein the top side of the middle portion comprises an adhesive; wherein the proximal end of the strip comprises the third of the three discrete sections, wherein the top surface of the proximal end comprises an adhesive; wherein the distal end of the strip is configured to be positioned proximate to the tick on skin, and further configured to be gradually moved in a distal direction underneath and in contact with the tick on the skin until at least a portion of the distal end of the strip is underneath the tick; wherein the strip is configured to fold at the two foldable indentations as the middle portion and proximal end of the strip are moved in a distal direction over the tick onto the distal end of the strip; wherein the adhesive on middle portion is configured to be pressed onto and adhere to the tick and the top surface of distal end of the strip; wherein the device is configured to permit the user to firmly pull the device and adhered tick straight up and away from the skin without the user physically touching the tick directly; wherein the top surface adhesive of the proximal end of the strip is configured to fold over and adhere to the tick and the bottom surface of the distal end of the strip; and wherein the device preserves the removed tick in a clear, viewable position for medical inspection and eventual disposal.

The subject invention also discloses a device configured to remove and encapsulate ticks, the device comprising: a substantially rigid strip comprising a substantially flat top surface, a substantially flat bottom surface, a distal end section, a proximal end section, and a foldable indentation between the distal end section and the proximal end section; wherein the proximal end section comprise adhesive on the top surface; wherein the distal end section of the strip is configured to be positioned proximate to the tick on skin, and further configured to be gradually moved in a distal direction underneath and in contact with the tick on the skin until at least a portion of the distal end section is underneath the tick; wherein the strip is configured to fold at the foldable indentation as the proximal end section is moved in a distal direction over the tick onto the distal end section; wherein the adhesive on the proximal end section is configured to be pressed onto and adhere to the tick and the top surface of distal end section; and wherein the device is configured to permit the user to firmly pull the device and adhered tick straight up and away from the skin.

The subject invention further discloses a device configured to remove and encapsulate ticks, the device comprising: a substantially rigid strip comprising a substantially flat top surface, a substantially flat bottom surface, a distal end section, a proximal end section, and a foldable indentation between the distal end section and the proximal end section; wherein the proximal end section comprise adhesive on the top surface; wherein the distal end section of the strip is configured to be positioned proximate to the tick on skin, and further configured to be gradually moved in a distal direction underneath and in contact with the tick on the skin until at least a portion of the distal end section is underneath the tick; wherein the strip is configured to fold at the foldable indentation as the proximal end section is moved in a distal direction over the tick onto the distal end section; wherein the adhesive on the proximal end section is configured to be pressed onto and adhere to the tick and the top surface of distal end section; and wherein the device is configured to permit the user to firmly pull the device and adhered tick straight up and away from the skin without the user physically touching the tick directly; and wherein the device preserves the removed tick in a clear, viewable position for medical inspection and eventual disposal.

The subject invention additionally discloses a device configured to remove and encapsulate ticks, the device comprising: a substantially rigid strip comprising a substantially flat top surface, a substantially flat bottom surface, two discrete sections, and a foldable indentation between the two discrete sections; wherein the proximal end discrete section comprise adhesive on the top surface; wherein the distal end of the strip is configured to be positioned proximate to the tick on skin, and further configured to be gradually moved in a distal direction underneath and in contact with the tick on the skin until at least a portion of the distal end is underneath the tick; wherein the strip is configured to fold at the foldable indentation as the proximal end discrete section is moved in a distal direction over the tick onto the distal end of the strip; wherein the adhesive on the proximal end discrete section is configured to be pressed onto and adhere to the tick and the top surface of distal end of the strip; and wherein the device is configured to permit the user to firmly pull the device and adhered tick straight up and away from the skin.

The subject invention discloses a device configured to remove and encapsulate ticks, the device comprising: a substantially rigid strip comprising a substantially flat top surface, a substantially flat bottom surface, two discrete sections, and a foldable indentation between the two discrete sections; wherein the proximal end discrete section comprise adhesive on the top surface; wherein the distal end of the strip is configured to be positioned proximate to the tick on skin, and further configured to be gradually moved in a distal direction underneath and in contact with the tick on the skin until at least a portion of the distal end is underneath the tick; wherein the strip is configured to fold at the foldable indentation as the proximal end discrete section is moved in a distal direction over the tick onto the distal end of the strip; wherein the adhesive on the proximal end discrete section is configured to be pressed onto and adhere to the tick and the top surface of distal end of the strip; and wherein the device is configured to permit the user to firmly pull the device and adhered tick straight up and away from the skin without the user physically touching the tick directly; and wherein the device preserves the removed tick in a clear, viewable position for medical inspection and eventual disposal.

The subject invention also discloses a tick removal and containment device comprising: a thin strip with a substantially flat top surface, a substantially flat bottom surface, a distal end, and a proximal end, wherein the thin strip comprises a substantially rigid first section and a substantially rigid second section separated by a foldable lateral indentation; wherein the first section is on the distal end of the thin strip and a proximal end of the first section comprises the foldable indentation, further wherein the first section comprises no adhesives; a notch on a distal end of the first section, wherein the notch comprises a substantially triangular shape; wherein a distal end of the second section comprises the foldable lateral indentation, wherein the top surface of the second section comprises an adhesive with a peelable flexible cover and a peel tab; wherein to remove a tick, the device is configured to be held in a user's hands with the notch positioned proximate to the tick on skin, wherein a tip of the triangular shaped notch is configured to be gradually moved in a distal direction underneath and in contact with the tick on the skin until at least a portion of the first section is underneath the tick; wherein once the first section is at least partially underneath the tick, the peelable flexible cover is removed from the second section using the peel tab; wherein the second section is configured to fold at the foldable lateral indentation in a distal direction over the tick onto the first section; wherein the exposed adhesive on the top surface of the second section is configured to be pressed onto and adhere to the tick and the top surface of first section; and wherein the device is configured to permit the user to firmly pull the device and adhered tick straight up and away from the skin.

The subject invention further discloses a tick removal and containment device comprising: a thin strip with a substantially flat top surface, a substantially flat bottom surface, a distal end, and a proximal end, wherein the thin strip comprises a substantially rigid first section and a substantially rigid second section separated by a foldable lateral indentation; wherein the first section is on the distal end of the thin strip and a proximal end of the first section comprises the foldable indentation, further wherein the first section comprises no adhesives; a notch on a distal end of the first section, wherein the notch comprises a substantially triangular shape; wherein a distal end of the second section comprises the foldable lateral indentation, wherein the top surface of the second section comprises an adhesive with a peelable flexible cover and a peel tab; wherein to remove a tick, the device is configured to be held in a user's hands with the notch positioned proximate to the tick on skin, wherein a tip of the triangular shaped notch is configured to be gradually moved in a distal direction underneath and in contact with the tick on the skin until at least a portion of the first section is underneath the tick; wherein once the first section is at least partially underneath the tick, the peelable flexible cover is removed from the second section using the peel tab; wherein the second section is configured to fold at the foldable lateral indentation in a distal direction over the tick onto the first section; wherein the exposed adhesive on the top surface of the second section is configured to be pressed onto and adhere to the tick and the top surface of first section; and wherein the device is configured to permit the user to firmly pull the device and adhered tick straight up and away from the skin without the user physically touching the tick directly; and wherein the device preserves the removed tick in a clear, viewable position for medical inspection and eventual disposal.

The subject invention additionally discloses a device configured to remove and encapsulate ticks, the device comprising: a substantially rigid thin strip comprising a substantially flat top surface, a substantially flat bottom surface, a distal end, a proximal end, two discrete sections, and a foldable indentation separating the two discrete sections; wherein the distal end of the thin strip comprises one of the two discrete sections and a notch configured to slide underneath and hold a tick; a proximal end portion of the thin strip comprising the other of the two discrete sections with one foldable indentation on the distal side of the proximal end portion, wherein the top surface of the proximal end portion comprises an adhesive; wherein the device is configured to be positioned with the notch proximate to the tick on skin, and further configured to permit the notch to be gradually moved in a distal direction underneath and in contact with the tick on the skin until at least a portion of the distal end of the thin strip is underneath the tick; wherein the thin strip is configured to fold at the foldable indentation as the proximal end portion of the thin strip are moved in a distal direction over the tick onto the distal end of the thin strip; wherein the adhesive on proximal end portion is configured to be pressed onto and adhere to the tick and the top surface of distal end of the thin strip; and wherein the device is configured to permit the user to firmly pull the device and adhered tick straight up and away from the skin.

The subject invention discloses a device configured to remove and encapsulate ticks, the device comprising: a substantially rigid thin strip comprising a substantially flat top surface, a substantially flat bottom surface, a distal end, a proximal end, two discrete sections, and a foldable indentation separating the two discrete sections; wherein the distal end of the thin strip comprises one of the two discrete sections and a notch configured to slide underneath and hold a tick; a proximal end portion of the thin strip comprising the other of the two discrete sections with one foldable indentation on the distal side of the proximal end portion, wherein the top surface of the proximal end portion comprises an adhesive; wherein the device is configured to be positioned with the notch proximate to the tick on skin, and further configured to permit the notch to be gradually moved in a distal direction underneath and in contact with the tick on the skin until at least a portion of the distal end of the thin strip is underneath the tick; wherein the thin strip is configured to fold at the foldable indentation as the proximal end portion of the thin strip are moved in a distal direction over the tick onto the distal end of the thin strip; wherein the adhesive on proximal end portion is configured to be pressed onto and adhere to the tick and the top surface of distal end of the thin strip; and wherein the device is configured to permit the user to firmly pull the device and adhered tick straight up and away from the skin; without the user physically touching the tick directly; and wherein the device preserves the removed tick in a clear, viewable position for medical inspection and eventual disposal.

The subject invention also discloses a method for removing and encapsulating a tick from skin, the method comprising: a) placing a distal end section of a strip device proximate to the tick, the strip device comprising a substantially rigid strip comprising a substantially flat top surface, a substantially flat bottom surface, the distal end section, a middle section, a proximal end section, a first foldable indentation between the distal end section and the middle section, and a second foldable indentation between the middle section and the proximal end section, wherein the middle section and the proximal end section comprise adhesive on the top surface; b) moving the strip device in a distal direction underneath and in contact with the tick on the skin until at least a portion of the distal end section is underneath the tick; c) folding the first and second foldable indentations; d) moving the middle section and the proximal end sections in a distal direction over the tick onto the distal end section; e) pressing the adhesive on the middle section onto the tick and the top surface of distal end section; f) pulling the strip device and the adhered tick straight up and away from the skin; g) folding the proximal end section over the tick; and h) adhering the proximal end section onto the bottom surface of the distal end section.

The subject invention further discloses a method for removing and encapsulating a tick from skin, the method comprising: a) placing a distal end section of a strip device proximate to the tick, the strip device comprising a substantially rigid strip comprising a substantially flat top surface, a substantially flat bottom surface, the distal end section, a middle section, a proximal end section, a first foldable indentation between the distal end section and the middle section, and a second foldable indentation between the middle section and the proximal end section, wherein the middle section and the proximal end section comprise adhesive on the top surface; b) moving the strip device in a distal direction underneath and in contact with the tick on the skin until at least a portion of the distal end section is underneath the tick; c) folding the first and second foldable indentations; d) moving the middle section and the proximal end sections in a distal direction over the tick onto the distal end section; e) pressing the adhesive on the middle section onto the tick and the top surface of distal end section; f) pulling the strip device and the adhered tick straight up and away from the skin without the user physically touching the tick directly; g) folding the proximal end section over the tick; and h) adhering the proximal end section onto the bottom surface of the distal end section to preserve the removed tick in a clear, viewable position for medical inspection and eventual disposal.

The subject invention additionally discloses a method for removing and encapsulating a tick from skin, the method comprising: a) positioning a distal end of a strip device proximate to the tick, the strip device comprising a substantially rigid strip comprising a substantially flat top surface, a substantially flat bottom surface, three discrete sections, and two foldable indentations between the three discrete sections, wherein the two of the three discrete sections comprise adhesive on the top surface; b) moving the strip device in a distal direction underneath and in contact with the tick on the skin until at least a portion of the distal end is underneath the tick; c) folding the two foldable indentations; d) moving two of the three discrete sections in a distal direction over the tick onto the distal end of the strip device; e) pressing the adhesive on the discrete sections onto the tick and the top and bottom surfaces of distal end of the strip device; and f) pulling the strip device and the adhered tick straight up and away from the skin.

The subject invention also discloses a method for removing and encapsulating a tick from skin, the method comprising: a) positioning a distal end of a strip device proximate to the tick, the strip device comprising a substantially rigid strip comprising a substantially flat top surface, a substantially flat bottom surface, three discrete sections, and two foldable indentations between the three discrete sections, wherein the two of the three discrete sections comprise adhesive on the top surface; b) moving the strip device in a distal direction underneath and in contact with the tick on the skin until at least a portion of the distal end is underneath the tick; c) folding the two foldable indentations; d) moving two of the three discrete sections in a distal direction over the tick onto the distal end of the strip device; e) pressing the adhesive on the discrete sections onto the tick and the top and bottom surfaces of distal end of the strip device; f) pulling the strip device and the adhered tick straight up and away from the skin without the user physically touching the tick directly; g) folding the proximal end section over the tick; and h) adhering the proximal end section onto the bottom surface of the distal end section to preserve the removed tick in a clear, viewable position for medical inspection and eventual disposal.

The subject invention discloses a method for removing and encapsulating a tick from skin, the method comprising: a) holding a strip device proximate to the tick in a user's hand, the strip device comprising a thin strip with a substantially flat top surface, a substantially flat bottom surface, a distal end, and a proximal end, wherein the thin strip comprises a substantially rigid first section, a substantially rigid second section, and a substantially rigid third section separated by first and second foldable lateral indentations, wherein the first section is on the distal end of the thin strip and a proximal end of the first section comprises the first foldable indentation, further wherein the first section comprises no adhesives, a notch on a distal end of the first section, wherein the notch comprises a substantially triangular shape, wherein a distal end of the second section comprises the first foldable lateral indentation, and a proximal end of the second section comprises the second foldable lateral indentation wherein the top surface of the second section comprises an adhesive with a first peelable flexible cover and a first peel tab, wherein the third section is on the proximal end of the thin strip, wherein a distal end of the third section comprises the second foldable lateral indentation, wherein the top surface of the third section comprises an adhesive with a second peelable flexible cover and a second peel tab; b) positioning a tip of the triangular shaped notch proximate to the tick; c) moving the triangular shaped notch in a distal direction underneath and in contact with the tick on the skin until at least a portion of the first section is underneath the tick; d) removing the first peelable flexible cover from the second section using the first peel tab; e) removing the second peelable flexible cover from the third section using the second peel tab; f) folding the second and third sections at the first and second foldable lateral indentations in a distal direction over the tick onto the first section; g) pressing the exposed adhesive the top surface of the second section onto the tick and the top surfaces of the first section; h) pulling the strip device and the adhered tick straight up and away from the skin; i) folding the third section over the tick at the second foldable lateral indentation in the distal direction; and j) pressing the exposed adhesive the top surface of the third section onto the tick and the bottom surface of the first section.

The subject invention additionally discloses a method for removing and encapsulating a tick from skin, the method comprising: a) holding a strip device proximate to the tick in a user's hand, the strip device comprising a thin strip with a substantially flat top surface, a substantially flat bottom surface, a distal end, and a proximal end, wherein the thin strip comprises a substantially rigid first section, a substantially rigid second section, and a substantially rigid third section separated by first and second foldable lateral indentations, wherein the first section is on the distal end of the thin strip and a proximal end of the first section comprises the first foldable indentation, further wherein the first section comprises no adhesives, a notch on a distal end of the first section, wherein the notch comprises a substantially triangular shape, wherein a distal end of the second section comprises the first foldable lateral indentation, and a proximal end of the second section comprises the second foldable lateral indentation wherein the top surface of the second section comprises an adhesive with a first peelable flexible cover and a first peel tab, wherein the third section is on the proximal end of the thin strip, wherein a distal end of the third section comprises the second foldable lateral indentation, wherein the top surface of the third section comprises an adhesive with a second peelable flexible cover and a second peel tab; b) positioning a tip of the triangular shaped notch proximate to the tick; c) moving the triangular shaped notch in a distal direction underneath and in contact with the tick on the skin until at least a portion of the first section is underneath the tick; d) removing the first peelable flexible cover from the second section using the first peel tab; e) removing the second peelable flexible cover from the third section using the second peel tab; f) folding the second and third sections at the first and second foldable lateral indentations in a distal direction over the tick onto the first section; g) pressing the exposed adhesive the top surface of the second section onto the tick and the top surfaces of the first section; h) pulling the strip device and the adhered tick straight up and away from the skin without the user physically touching the tick directly; i) folding the third section over the tick at the second foldable lateral indentation in the distal direction; and j) pressing the exposed adhesive the top surface of the third section onto the tick and the bottom surface of the first section to preserve the removed tick in a clear, viewable position for medical inspection and eventual disposal.

The subject invention discloses a method for removing and encapsulating a tick from skin, the method comprising: a) holding a strip device proximate to the tick in a user's hand, the strip device comprising a substantially rigid thin strip comprising a substantially flat top surface, a substantially flat bottom surface, a distal end, a proximal end, three discrete sections, and two foldable indentations separating the three discrete sections, wherein the distal end of the thin strip comprises one of the three discrete sections and a notch configured to slide underneath and hold a tick; a middle portion of the thin strip comprising another of the three discrete sections with one foldable indentation on the distal side of the middle portion and the other foldable indentation on the proximal side, wherein the top surface of the middle portion comprises an adhesive, wherein the proximal end of the thin strip comprises the third of the three discrete sections, wherein the top surface of the proximal end comprises an adhesive; b) positioning the notch proximate to the tick; c) moving the notch in a distal direction underneath and in contact with the tick on the skin until at least a portion of the distal end of the thin strip is underneath the tick; d) folding the two foldable indentations; e) moving the middle portion and proximal end of the strip in a distal direction over the tick onto the distal end of the thin strip; f) pressing the exposed adhesive the top surface of the middle portion onto the tick and the top surfaces of distal end of the thin strip; g) pulling the strip device and the adhered tick straight up and away from the skin; h) folding the third section over the tick at the second foldable lateral indentation in the distal direction; and i) pressing the exposed adhesive the top surface of the proximal end of the thin strip onto the tick and the bottom surface of the first section.

The subject invention further discloses a method for removing and encapsulating a tick from skin, the method comprising: a) holding a strip device proximate to the tick in a user's hand, the strip device comprising a substantially rigid thin strip comprising a substantially flat top surface, a substantially flat bottom surface, a distal end, a proximal end, three discrete sections, and two foldable indentations separating the three discrete sections, wherein the distal end of the thin strip comprises one of the three discrete sections and a notch configured to slide underneath and hold a tick; a middle portion of the thin strip comprising another of the three discrete sections with one foldable indentation on the distal side of the middle portion and the other foldable indentation on the proximal side, wherein the top surface of the middle portion comprises an adhesive, wherein the proximal end of the thin strip comprises the third of the three discrete sections, wherein the top surface of the proximal end comprises an adhesive; b) positioning the notch proximate to the tick; c) moving the notch in a distal direction underneath and in contact with the tick on the skin until at least a portion of the distal end of the thin strip is underneath the tick; d) folding the two foldable indentations; e) moving the middle portion and proximal end of the strip in a distal direction over the tick onto the distal end of the thin strip; f) pressing the exposed adhesive the top surface of the middle portion onto the tick and the top surfaces of distal end of the thin strip; g) pulling the strip device and the adhered tick straight up and away from the skin without the user physically touching the tick directly; h) folding the third section over the tick at the second foldable lateral indentation in the distal direction; and i) pressing the exposed adhesive the top surface of the proximal end of the thin strip onto the tick and the bottom surface of the first section to preserve the removed tick in a clear, viewable position for medical inspection and eventual disposal.

The subject invention additionally discloses a method for removing and encapsulating a tick from skin, the method comprising: a) positioning a distal end section of a strip device proximate to the tick, the strip device comprising a substantially rigid strip comprising a substantially flat top surface, a substantially flat bottom surface, the distal end section, a proximal end section, and a foldable indentation between the distal end section and the proximal end section, wherein the proximal end section comprises adhesive on the top surface; b) moving the distal end section in a distal direction underneath and in contact with the tick on the skin until at least a portion of the distal end section of the thin strip is underneath the tick; c) folding the foldable indentation; d) moving the proximal end section of the strip in a distal direction over the tick onto the distal end section of the rigid strip; e) pressing the exposed adhesive the top surface of the proximal end section onto the tick and the top surface of distal end section of the rigid strip; and f) pulling the strip device and the adhered tick straight up and away from the skin without the user physically touching the tick directly to preserve the removed tick in a clear, viewable position for medical inspection and eventual disposal.

In further embodiments of the subject invention, the devices and methods permit removal of a tick without the user physically touching the tick.

In embodiments of the subject invention, the devices and methods preserve the removed tick in a clear, viewable position for medical inspection and eventual disposal.

In further embodiments of the subject invention, the adhesives may comprise a hypoallergenic pressure-sensitive adhesive layer.

In embodiments of the subject invention, the devices may include a tick attractant.

In further embodiments of the subject invention, the devices may be substantially circular, substantially oval, or substantially elliptical.

There have thus been broadly outlined important features of the invention in order that the detailed description thereof that follows may be better understood, and in order that the present contribution to the art may be better appreciated. There are additional features of the invention that will be described hereinafter and which will form the subject matter of the claims appended hereto. These together with other embodiments of the invention, and with various features of novelty which characterize the invention, are pointed out with particularity in the claims annexed to and formed as part of this disclosure.

The term "substantially" is defined as at least close to (and can include) a given value or state, as understood by a person of ordinary skill in the art. In one embodiment, the term "substantially" refers to ranges within 10%, preferably within 5%, more preferably within 1%, and most preferably within 0.1% of the given value or state being specified.

For a conceptual understanding of the invention and its operational advantages, refer to the accompanying drawings and descriptive matter in which there are preferred embodiments of the invention illustrated. Other features and advantages of the present invention will become apparent from the following description of the preferred embodiment(s), taken in conjunction with the accompanying drawings, which by way of example; illustrate the principles of the invention.

BRIEF DESCRIPTION OF THE DRAWINGS

Advantages of the present invention will be apparent from the following detailed description of exemplary embodiments thereof, which description should be considered in conjunction with the accompanying drawings.

DETAILED DESCRIPTION OF EMBODIMENTS

Figure 1:
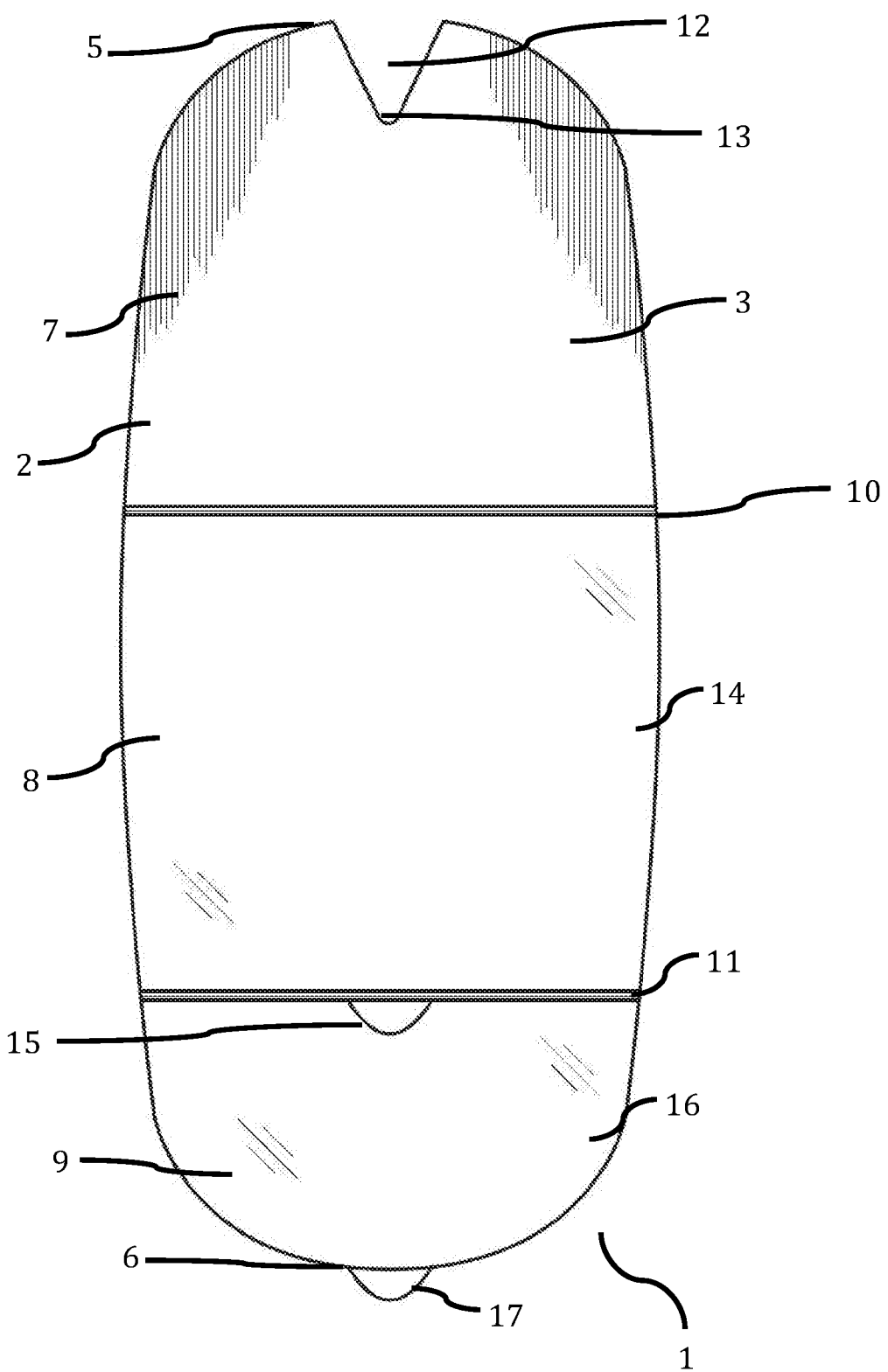
FIG. 1 illustrates a top view of one embodiment of the tick removal and disposal device in the open configuration.
Figure 2:
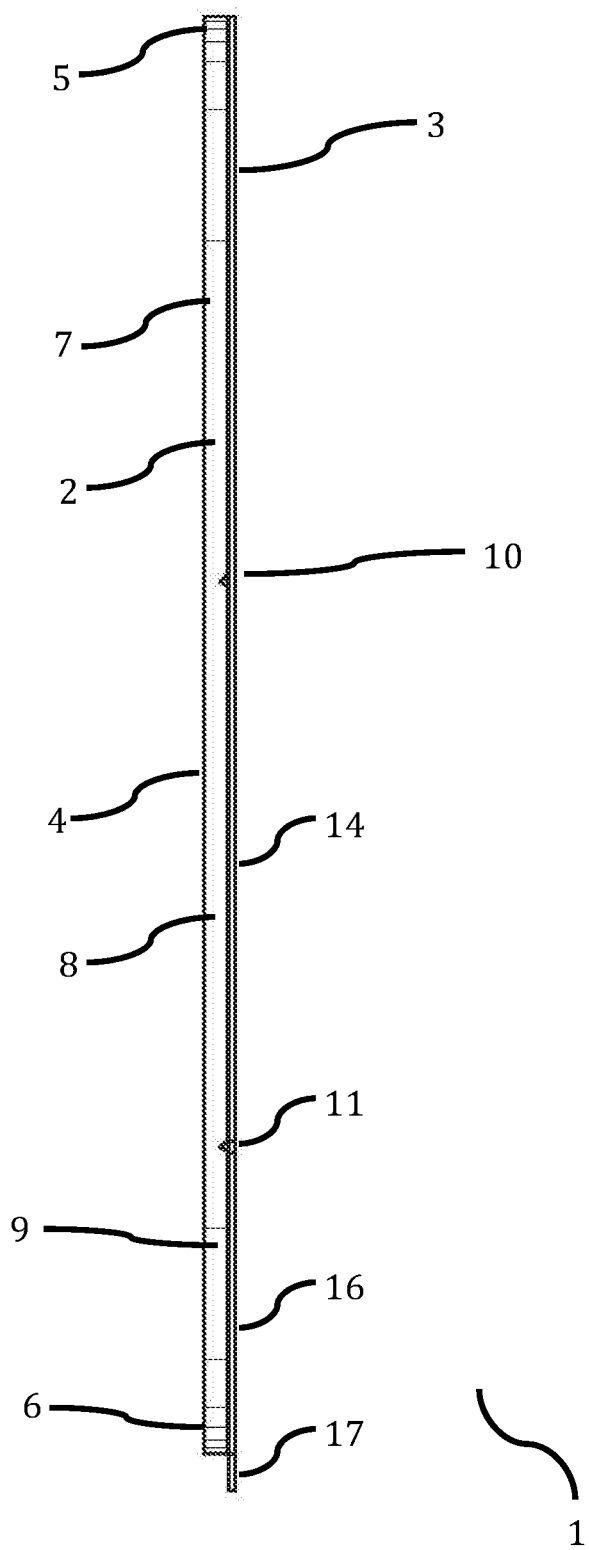
FIG. 2 illustrates a side view of one embodiment of the tick removal and encapsulation device in the open configuration.
Figure 3:
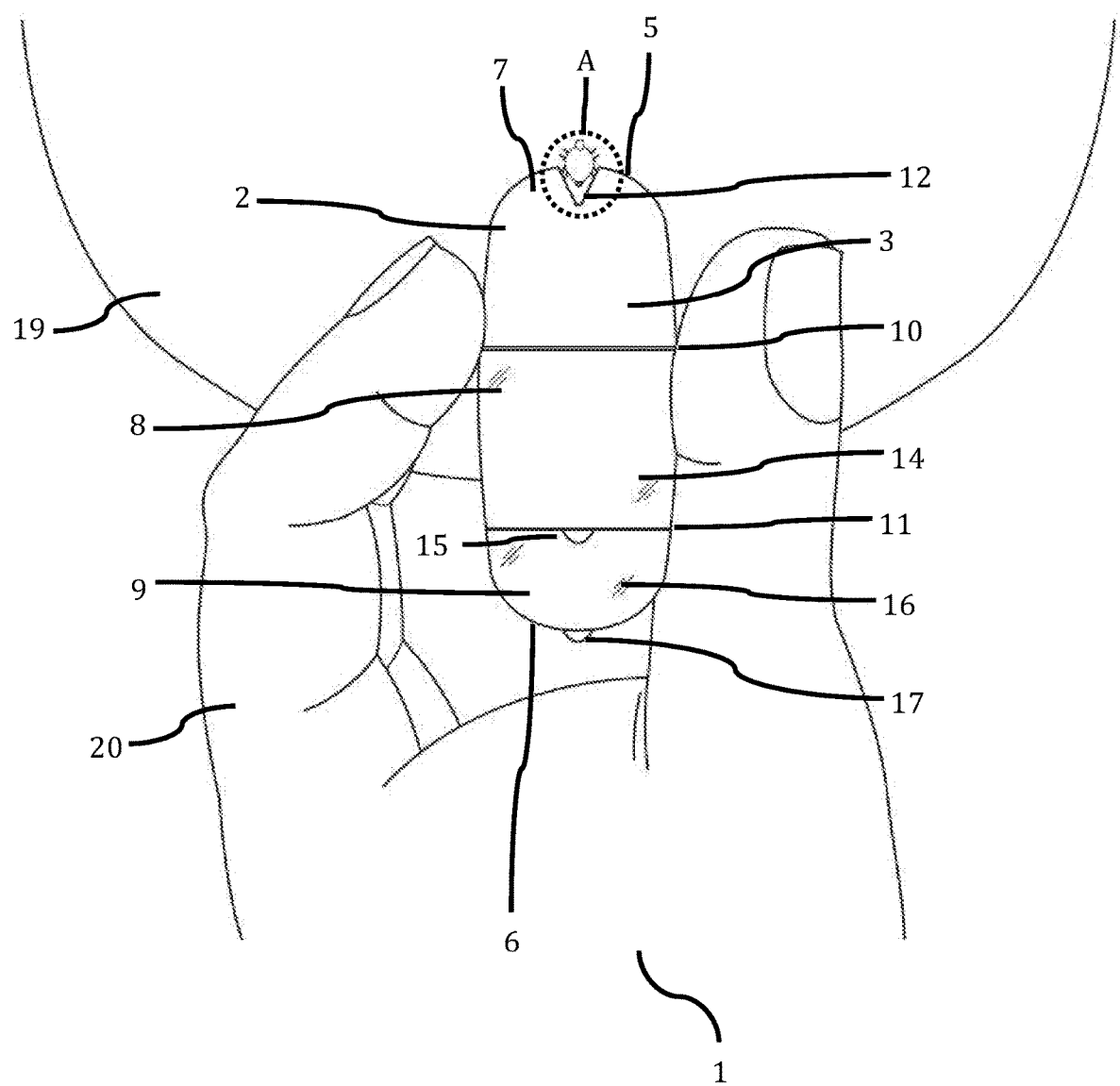
FIG. 3 illustrates a top view of one embodiment of the tick removal and encapsulation device in the open configuration being positioned under a tick on a user's knee.
Figure 4:
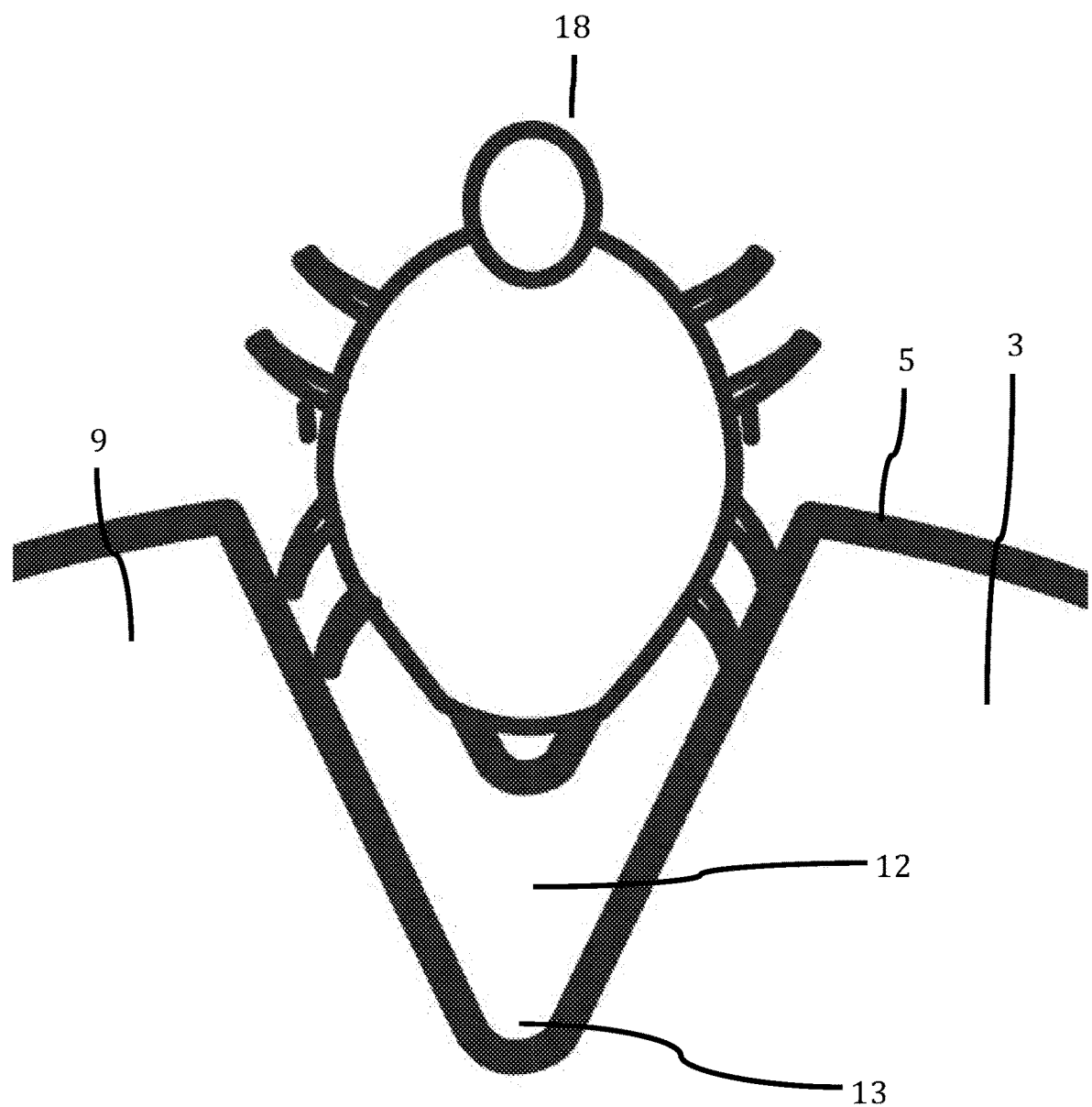
FIG. 4 illustrates an enlarged top view of line A of FIG. 3 of the tick removal and encapsulation device in the open configuration being positioned under the tick on the user's knee.
Figure 5:
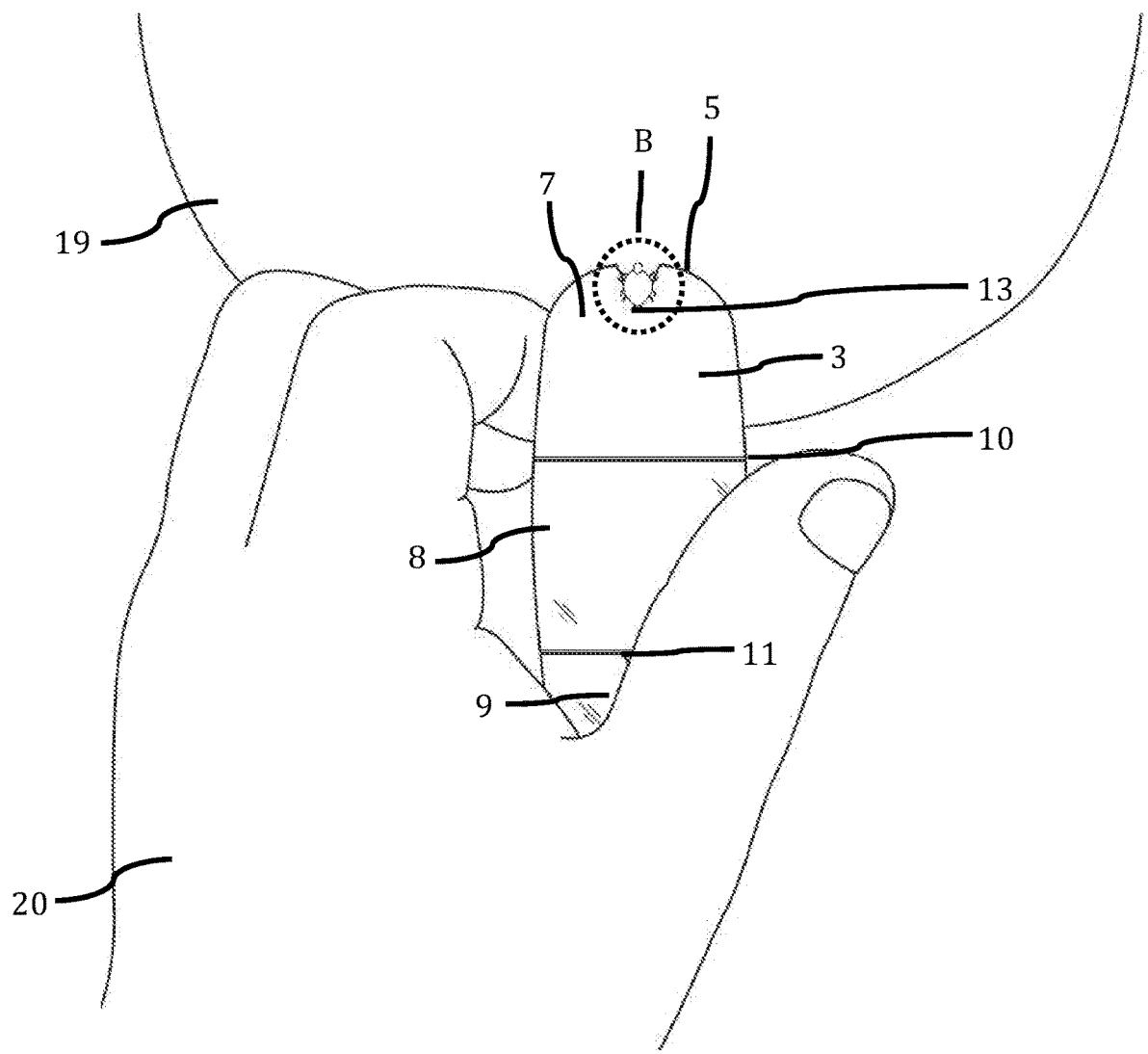
FIG. 5 illustrates a top view of one embodiment of the tick removal and encapsulation device in the open configuration inserted under the tick on the user's knee.
Figure 6:
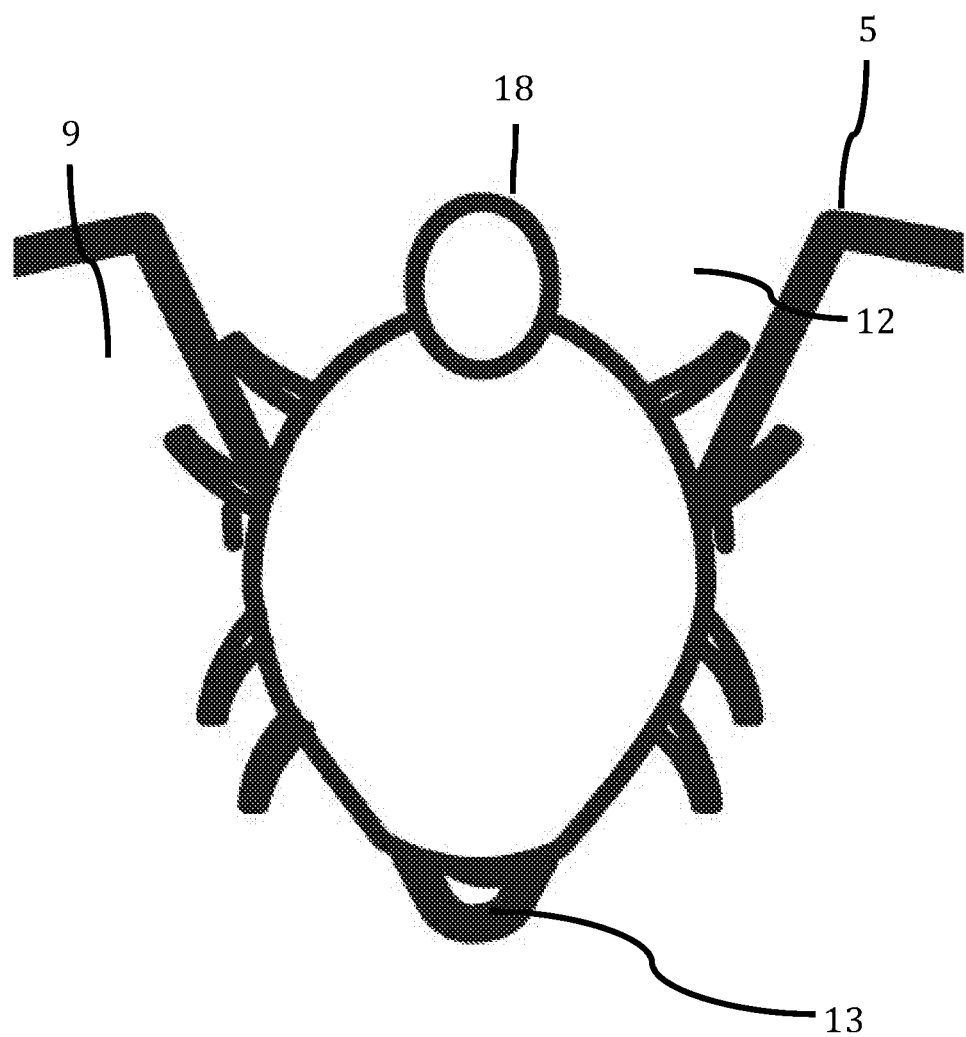
FIG. 6 illustrates an enlarged top view of line B of FIG. 5 of the tick removal and encapsulation device in the open configuration inserted under the tick on the user's knee.

The following will describe, in detail, several embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

The subject invention discloses a tick removal and encapsulation device 1 and method using a thin strip 2. In embodiments of the subject invention, the thin strip 2 is seven to sixteen centimeters in length, with a preferred embodiment of eleven and one-half centimeters in length. In further embodiments of the subject invention, the thin strip 2 is four to eight centimeters in maximum width, with a preferred embodiment of five centimeters in maximum width. In additional embodiments of the subject invention, the thin strip 2 is 0.05 millimeters to twenty millimeters in thickness.

As illustrated in FIGS. 1, 2, 10, and 11, the thin strip 2 comprises a substantially flat top side 3, a substantially flat bottom side 4, a curved distal end 5, and a curved proximal end 6. The think strip 2 comprises three sections 7, 8, 9 separated by two foldable indentations 10, 11.

The first section 7 is on the distal end 5 of the strip 2, and comprises a notch 12 on the distal end 5. In the preferred embodiment, the notch 12 comprises a substantially open triangular shape with the tip 13 of the triangular shape away from the distal end 5. In further embodiments of the subject invention, the notch 12 may substantially comprise other open shapes, included, but not limited to: substantially circular, half-circular, ellipse, oval, half-oval, square, rectangle, trapezoid, pentagon, half-pentagon, hexagon, half-hexagon, heptagon, octagon, half-octagon, nonagon, or decagon. The first section 7 of the strip 2 is composed of substantially rigid, substantially transparent or clear, plastic or other PVC known to those skilled in the art. The first section 7 comprises no adhesives on the bottom 4 or top 3 sides. In embodiments of the subject invention, the first section 7 is three to six centimeters in length, with a preferred embodiment of four and one-half centimeters in length. In further embodiments of the subject invention, the first section 7 is four to eight centimeters in maximum width at the foldable indentation 10, with a preferred embodiment of five centimeters in maximum width. In additional embodiments of the subject invention, the first section 7 is two to four centimeters in width at distal end 5, with a preferred embodiment of three centimeters in width.

The second section 8 is between foldable indentations 10, 11 and the first section 7 and the third section 9. The second section 8 of the strip 2 is composed of semi-rigid, semi-flexible, substantially transparent or clear, plastic or other PVC known to those skilled in the art. The top side 3 of the second section 8 comprises an adhesive. The adhesive on the top side 3 of the second section 8 is covered with a peelable flexible first cover 14. The first cover 14 is composed of flexible, substantially transparent or clear, plastic or other PVC known to those skilled in the art. The first cover 14 comprises a peel tab 15 for removing the first cover 14 from the second section 8 to expose the adhesive on the top side 3 of the second section 8. In embodiments of the subject invention, the second section 8 is three to eight centimeters in length, with a preferred embodiment of five centimeters in length. In further embodiments of the subject invention, the second section 8 is four to eight centimeters in maximum width, with a preferred embodiment of five centimeters in maximum width.

The third section 9 is on the proximal end 6 of the strip 2. The third section 9 of the strip 2 is composed of semi-rigid, semi-flexible, substantially transparent or clear, plastic or other PVC known to those skilled in the art. The top side 3 of the third section 9 comprises an adhesive. The adhesive on the top side 3 of the third section 9 is covered with a second peelable flexible cover 16. The second cover 16 is composed of flexible, substantially transparent or clear, plastic or other PVC known to those skilled in the art. The second cover 16 comprises a peel tab 17 on the proximal end 6 for removing the second cover 16 from the third section 9 to expose the adhesive on the top side 3 of the third section 9. In embodiments of the subject invention, the third section 9 is one to three centimeters in length, with a preferred embodiment of one and one half centimeters in length. In further embodiments of the subject invention, the third section 9 is four to eight centimeters in maximum width at the foldable indentation 11, with a preferred embodiment of five centimeters in maximum width. In additional embodiments of the subject invention, the third section 9 is two to four centimeters in width at proximal end 6, with a preferred embodiment of three centimeters in width.

In embodiments of the subject invention, the first section, the second section 8, and the third section 9 may have rigidity analogous to that of a conventional index card, or stronger rigidity similar to that of cardboard or rigid plastic. In other embodiments of the subject invention, the first section, the second section 8, and the third section 9 may be opaque to minimize viewing due to user fear of insects.

In embodiments of the subject invention, the adhesives used on the strip 2 may comprise similar properties to those adhesives found on conventional clear cellophane tapes, masking tapes, sticky notes, pressure sensitive adhesives which form a bond on contact, strong tacky adhesives, non-drying adhesives, removable adhesives, and permanent non-removable adhesives. In further embodiments of the subject invention, distribution of the adhesive on the thin strip may be provided in a wide variety of manners which would not effect the performance of the device.

In embodiments of the subject invention, the flexible first covers 14 and 16 placed on top of the adhesive can be any flexible material which seals the adhesive, prevents the adhesive from drying out, and prevents it from adhering to extraneous matter until the strip 2 is ready for use.

The tick removal and encapsulation device 1 is used as illustrated in FIGS. 3-12. The device 1 is held in a user's hand 20, and the notch 12 on the distal end 5 of the device is positioned proximate and underneath a tick 18 on the skin 19. The tip 13 and the substantially open triangular shape of the notch 12 are gradually moved in a distal direction underneath and in contact with the tick 18 on the skin 19. The substantially rigid material of first section 7 enables the user to firmly and gradually insert it underneath the tick 18.

Figure 7:
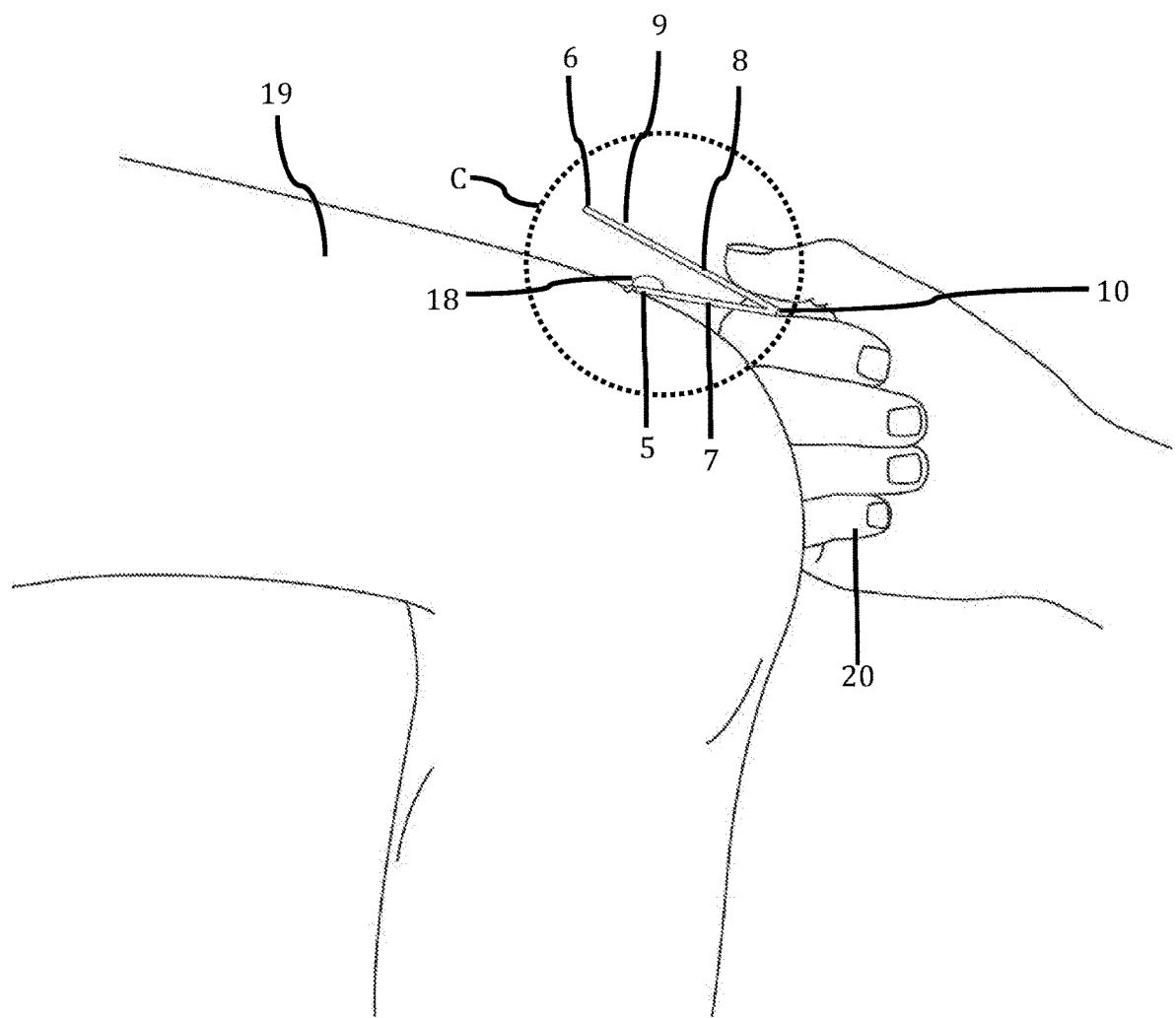
FIG. 7 illustrates a side view of one embodiment of the tick removal device and encapsulation in the partially folded configuration inserted under the tick on the user's knee.
Figure 8:
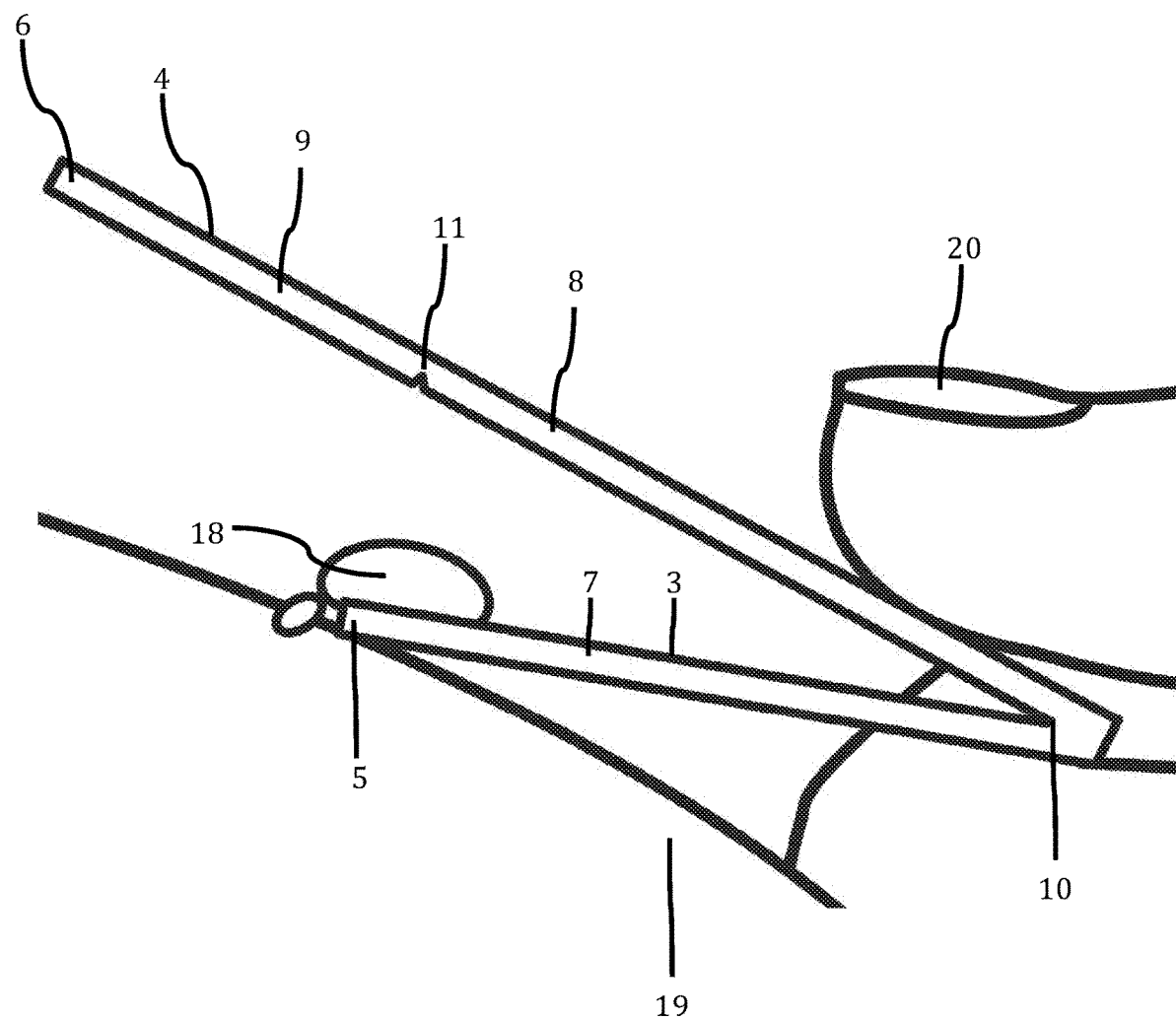
FIG. 8 illustrates an enlarged side view of line C of FIG. 7 of the tick removal and encapsulation device in the partially folded configuration inserted under the tick on the user's knee.

As illustrated in FIGS. 7 and 8, once the first section 7 is underneath the tick 18, the first peelable flexible first cover 14 is removed from the second section 8 using the first peel tab 15, and the second peelable flexible cover 16 is removed from the third section 9 using the second peel tab 17. This removal of the first and second peelable flexible covers 14, 15 exposes the top adhesive side 3 of second section 8 and third section 9. Once the first and second peelable flexible covers 14, 15 are removed, the second section 8 and the third section 9 are both folded at indentation 10 over the tick 18 and the first section 7.

Figure 9:
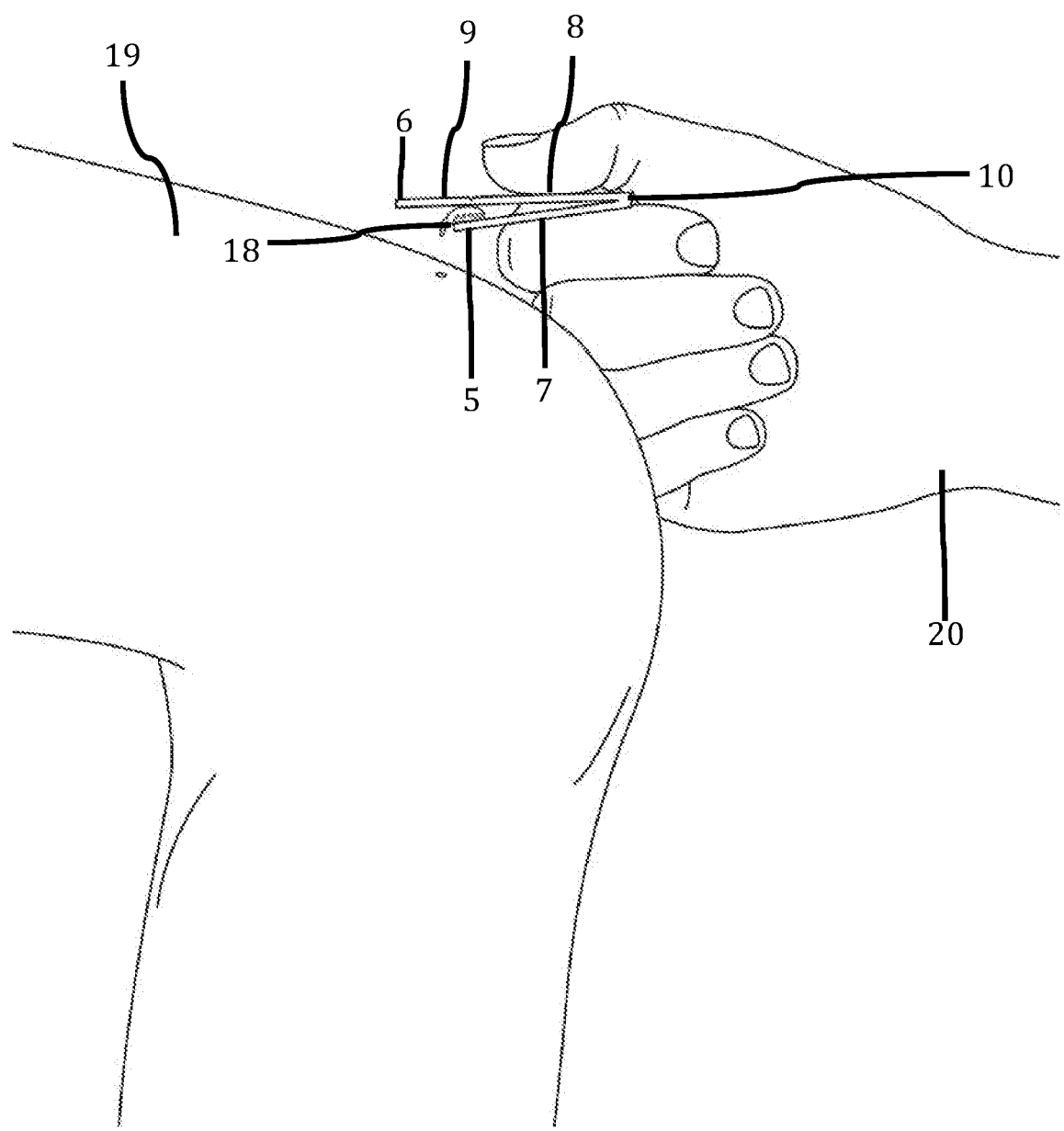
FIG. 9 illustrates a side view of one embodiment of the tick removal and encapsulation device in the partially folded configuration holding the tick removed the user's knee.
Figure 10:
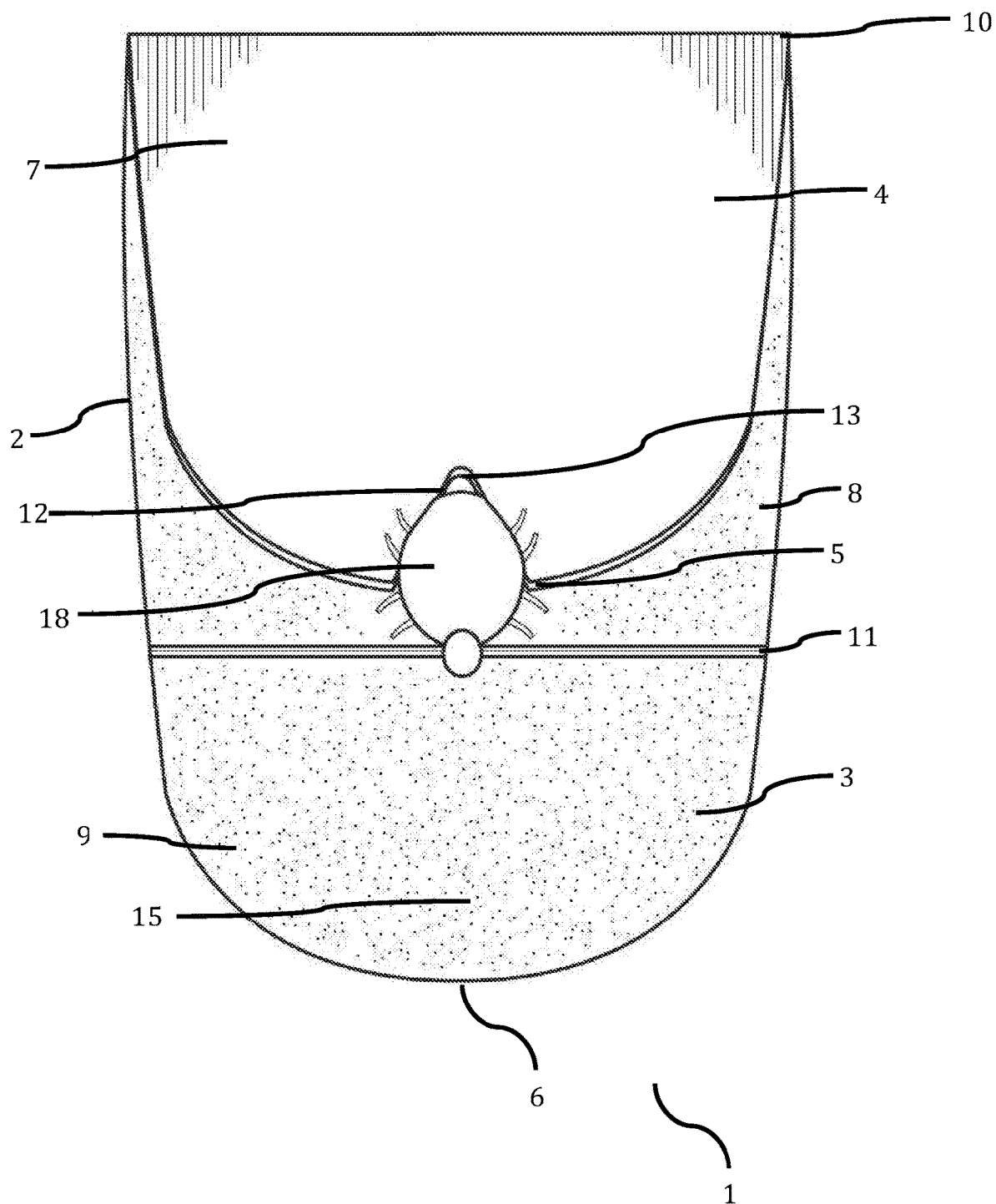
FIG. 10 illustrates a bottom view of one embodiment of the tick removal and encapsulation device in the partially folded configuration holding the tick.

As illustrated in FIGS. 9 and 10, once the second section 8 and the third section 9 are both folded at indentation 10 over the tick 18 and the first section 7. The exposed top adhesive side 3 of second section 8 is pressed onto the tick 15 and top side 3 of first section 7. This adheres the tick 18 between the top side 3 of the folded second section 8 and the top side 3 of the first section 7. At this point, the user firmly pulls the tick 18 straight up and away from the skin 19.

Figure 11:
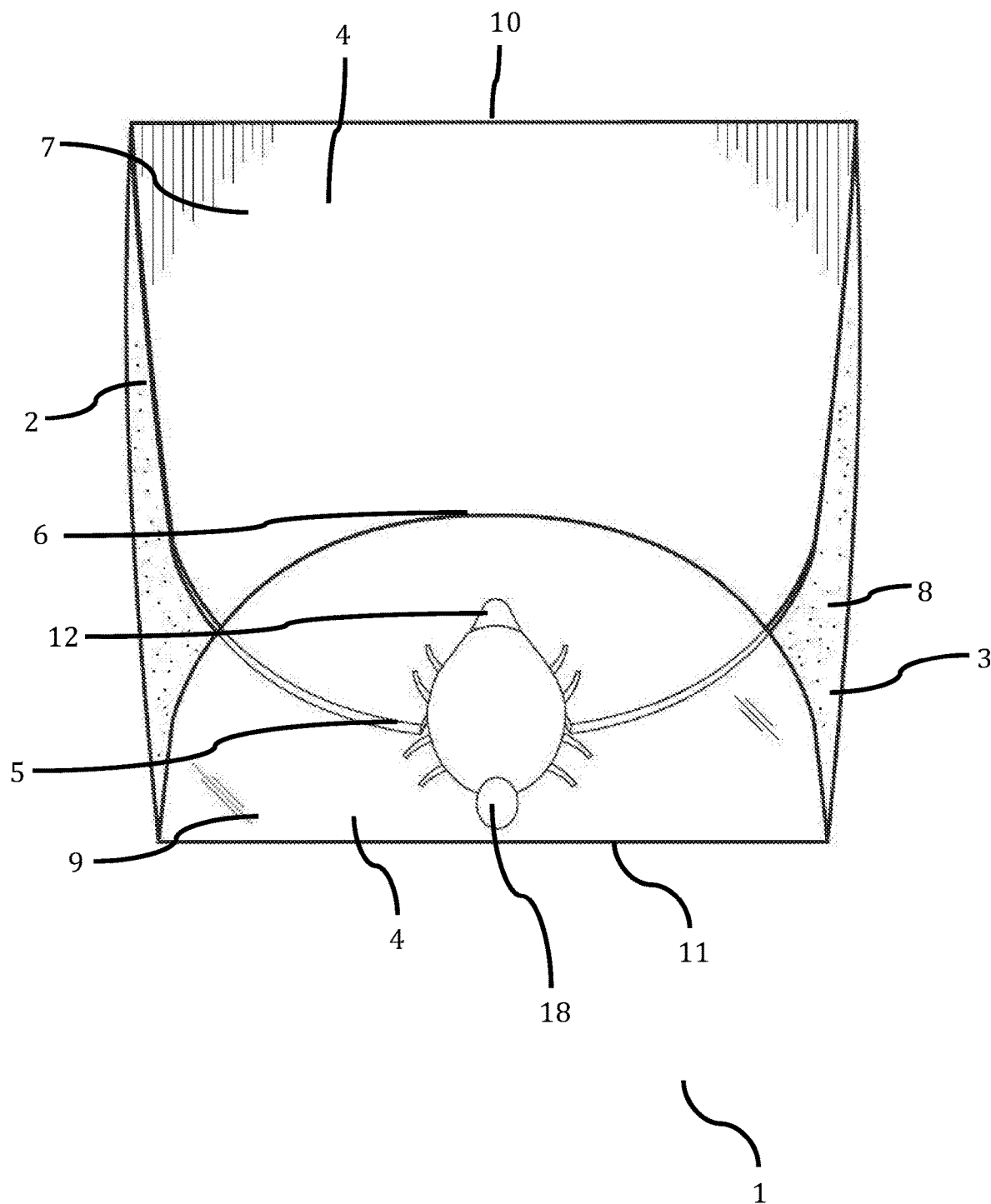
FIG. 11 illustrates a bottom view of one embodiment of the tick removal and encapsulation device in the fully folded configuration holding the tick.
Figure 12:
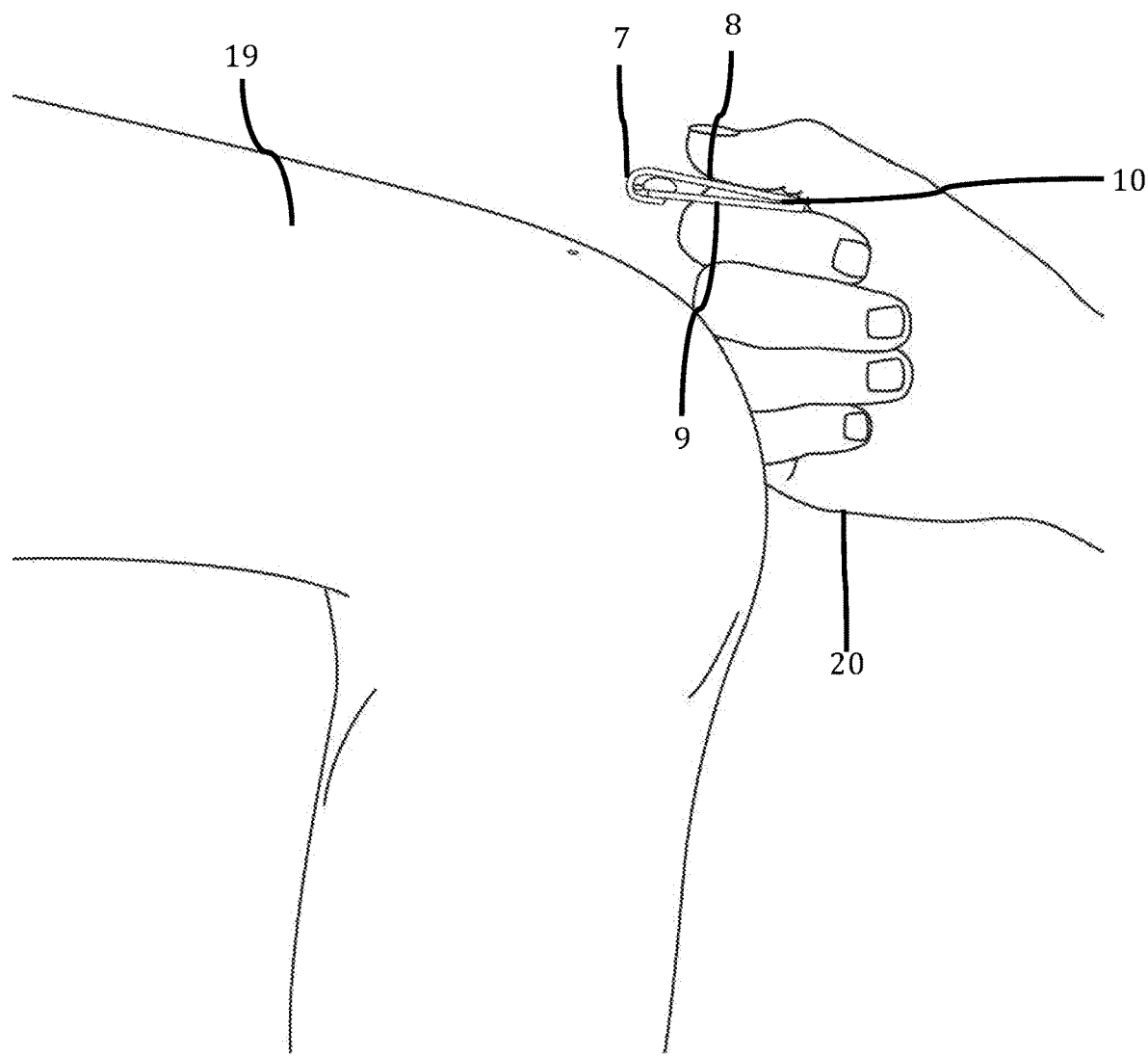
FIG. 12 illustrates a side view of one embodiment of the tick removal and encapsulation device in the fully folded configuration holding the tick.

As illustrated in FIGS. 11 and 12, once the tick is adhered between the top side 3 of the folded second section 8 and the top side 3 of the first section 7, the exposed top adhesive side 3 of the third section 9 is folded over and pressed onto the tick 18 and the bottom side 4 of first section 7 at indentation 11. This comprises and preserves the tick for viewing between first section 7, second section 8, and third section 9 with an adhesive surface at the bottom of the tick 18 from the top side of second section 8 and an adhesive surface at the top of the tick 18 from the top side of third section 9.

The tick 18 is now preserved and secured within the clear and transparent folded device 1 in a clear, viewable position. The tick 18 may now be safely transported to medical personnel for inspection and possibly testing of the tick 18 for any diseases that may have been passed to the animal or human hosts, so preventative treatment measures can be determined and implemented. The tick 18 is not exposed to surroundings for possible accidental physical contact by humans and animals during transport, viewing, and testing.

The many aspects and benefits of the invention are apparent from the detailed description, and thus, it is intended for the following claims to cover such aspects and benefits of the invention, which fall within the scope, and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A device configured to remove and encapsulate ticks, the device comprising:

a substantially rigid strip comprising a substantially flat top surface, a substantially flat bottom surface, a curved distal end section, a substantially triangular shaped notch contained within the curved distal end section, a middle section, a curved proximal end section, a first foldable indentation between the distal end section and the middle section, and a second foldable indentation between the middle section and the proximal end section;

wherein the middle section and the proximal end section comprise adhesive on the top surface;

wherein the triangular shaped notch is configured to be positioned proximate to the tick on skin, and further configured to be gradually moved in a distal direction underneath and in contact with the tick on the skin until at least a portion of the triangular shaped notch is underneath the tick;

wherein the strip is configured to fold at the first and second foldable indentations as the middle section and the proximal end section are moved in a distal direction over the tick onto the triangular shaped notch;

wherein the adhesive on the middle section is configured to be pressed onto and adhere to the tick and the top surface of the triangular shaped notch;

wherein the device is configured to permit a user to firmly pull the device and adhered tick straight up and away from the skin; and wherein the adhesive on the proximal end section is configured to fold over and adhere to the tick and the bottom surface of the triangular shaped notch of the strip.

2. The device of claim 1, wherein the device is configured to remove a tick without the user physically touching the tick.

3. The device of claim 1, wherein the device is configured to preserve a tick in a viewable position for medical inspection and eventual disposal.

4. The device of claim 1, wherein the adhesive comprises a hypoallergenic pressure-sensitive adhesive layer.

5. The device of claim 1, wherein the strip comprises a length of seven to sixteen centimeters.

6. The device of claim 1, wherein the strip comprises a width of four to eight centimeters.

7. The device of claim 1, wherein the strip includes a tick attractant.

8. The device of claim 1, wherein the strip is composed of substantially transparent plastic.

9. The device of claim 1, wherein the strip comprises a shape selected from the group consisting of substantially circular, substantially oval, and substantially elliptical.

* * * * *